United States Patent [19]

Chen et al.

[11] Patent Number: 5,169,878
[45] Date of Patent: Dec. 8, 1992

[54] COMPOSITION AND METHOD OF PREPARATION OF VISCOSITY-STABILIZED POLYISOCYANATES COMPRISING TRIAZINE GROUPS

[75] Inventors: Lao-Jer Chen; Steven B. Lowenkron, both of Houston; Shenghong A. Dai, Lake Jackson, all of Tex.

[73] Assignee: The Dow Chemical Company, Midland, Mich.

[21] Appl. No.: 682,509

[22] Filed: Apr. 8, 1991

[51] Int. Cl.$^5$ .............................................. C08G 18/73
[52] U.S. Cl. ........................................ 521/161; 528/73; 252/182.2; 252/182.21; 544/194
[58] Field of Search ............... 544/194; 252/182.2, 252/182.21; 521/161; 528/73

[56] References Cited

U.S. PATENT DOCUMENTS

| | | | |
|---|---|---|---|
| 3,728,289 | 4/1973 | Reuter et al. | 521/161 |
| 3,745,134 | 7/1973 | Fensch | 521/160 |
| 4,193,932 | 3/1980 | Zamamota et al. | 260/453 |
| 4,294,719 | 10/1981 | Wagner et al. | 252/182 |
| 4,424,284 | 1/1984 | Patton, Jr. et al. | 521/99 |
| 4,699,933 | 10/1987 | Hefner, Jr. et al. | 521/166 |

OTHER PUBLICATIONS

R. Richter & H. Ulrich, Two Synthetic Routes to 1,3,5-Triaryl-2-Phenylimino-4,6-Dioxohexahydro-S-Triazines, 22 Tetrahedron Letters 1875-78 (1974).

*Primary Examiner*—Maurice J. Welsh
*Assistant Examiner*—Rachel Johnson

[57] ABSTRACT

A viscosity-stable polyisocyanate prepared by heating a polyisocyanate containing uretone imine groups and a catalyst under reaction conditions sufficient to produce compounds containing 2-imino-4,6-dioxohexahydro-s-triazine groups is disclosed. The polyisocyanate product so prepared may be used alone or blended with other polyisocyanates or diisocyanates to produce polyurethane, polyisocyanurate, polyamide and related polymers. These polymers, when used to prepare a foam, may exhibit improved dimensional stability and flammability. Also disclosed is a family of isocyanate compounds containing at least one 2-imino-4,6-dioxohexahydro-s-triazine group and having an isocyanate functionality of at least 4.

19 Claims, No Drawings

COMPOSITION AND METHOD OF PREPARATION OF VISCOSITY-STABILIZED POLYISOCYANATES COMPRISING TRIAZINE GROUPS

BACKGROUND OF THE INVENTION

This invention relates to a composition of polyisocyanates which increase in viscosity more slowly and/or to a lesser extent than other known polyisocyanates. This invention also relates to a method for preparing such polyisocyanates.

Polymeric isocyanates, particularly polymeric methylene diphenyl diisocyanate (sometimes also referred to as polymethylene polyphenylisocyanate, hereinafter PMDI) are very useful polymeric intermediate materials. Used primarily as components in rigid polyurethane and polyisocyanurate foams, polymeric isocyanates are particularly valued for their excellent insulating properties. These insulating foams may be found in applications ranging from home construction to ice chests and refrigerators and even to industrial applications such as pipe and vessel insulation.

However, using PMDI is not trouble-free. It is well known in the art that polyisocyanates, particularly those polyisocyanates which are commercially available (hereinafter conventional polyisocyanates), such as PMDI, increase in viscosity during storage. This is one of the reasons that PMDI typically has a shelf life of about 6 months. PMDI, when stored longer than its shelf life, may become too viscous for its intended application. It is therefore desirable to prepare a PMDI which increases in viscosity more slowly than conventional polyisocyanates.

Since PMDI, in the form of polyurethane or polyisocyanurate foam, is often used in construction, PMDI based foams are required to meet very strict flammability specifications. These flammability specifications limit the amount of heat and smoke which may be released when a foam is exposed to heat and/or flame. However, it is difficult to meet flammability specifications with PMDI based carbon dioxide blown or carbon dioxide/chlorofluorocarbon co-blown foams. A blowing agent is a material which vaporizes or otherwise produces gas during the forming of a foam and thereby serves to reduce the density of the foam. Some blowing agents such as the chlorofluorocarbon compounds, also contribute to the insulative capability of the foam and reduce flammability. Chlorofluorocarbons have long been used as blowing agents for PMDI based foams. However, due to environmental considerations, the use of chlorofluorocarbons has been increasingly discouraged and use of alternative blowing agents has been found to be desirable.

An example of an alternative type of blowing agent is carbon dioxide. Foams produced with blowing additives which generate carbon dioxide blowing agents are considered environmentally superior to foams prepared utilizing only chlorofluorocarbon blowing agents. A disadvantage of using carbon dioxide producing blowing additives to prepare PMDI foams is that carbon dioxide blown foams often have inferior flammability properties when compared with foams blown with chlorofluorocarbons. It is, therefore, also desirable to prepare a polyisocyanate which, when used to prepare a foam, has improved flammability properties when compared with conventional PMDI, especially when utilized in preparing a carbon dioxide blown foam.

SUMMARY OF THE INVENTION

In one aspect, this invention is a method for preparing liquid polymeric isocyanates which increase in viscosity more slowly and to a lesser extent than conventional polyisocyanates. This method comprises heating an admixture of a polyisocyanate containing uretone imine groups and a catalyst under reaction conditions sufficient to form compounds containing 2-imino-4,6-dioxohexahydro-s-triazine groups.

A composition of a polyisocyanate containing 2-imino-4,6-dioxohexahydro-s-triazine groups which increases in viscosity more slowly and to a lesser extent than conventional polyisocyanates, for use in preparing a polyurea, polyamide, polyurethane, or polyisocyanurate is also an aspect of this invention.

Another aspect of this invention is a polymer prepared by reacting a material containing active hydrogen containing groups with a polyisocyanate containing 2-imino-4,6-dioxohexahydro-s-triazine groups prepared by the method of this invention.

Blends of the liquid polyisocyanates of this invention with isocyanates and polyisocyanates are also aspects of this invention. Blends may be from about 1 weight percent to about 99 weight percent of the polyisocyanate containing 2-imino-4,6-dioxohexahydro-s-triazine groups prepared by the present invention.

In another aspect, this invention includes compounds of the general formula:

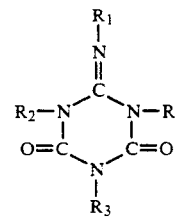

wherein

R, $R_1$, $R_2$, and $R_3$ are independently selected from the group consisting of:

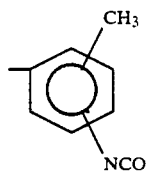

and

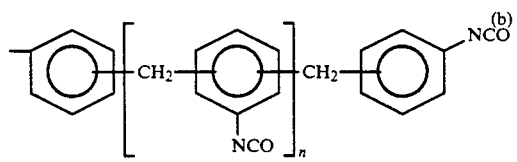

wherein n is an integer from 0 to 4 inclusive.

One utility of the present invention is to prepare polyisocyanates which increase in viscosity more slowly and to a lesser extent than conventional polyisocyanates. Another utility of the present invention is that these viscosity-stable polyisocyanates can be used to prepare chlorofluorocarbon-free or reduced foams which have improved flammability and dimensional stability properties as compared to similar foams prepared with conventional polyisocyanates.

DESCRIPTION OF THE PREFERRED EMBODIMENTS

The first requirement of the present invention is a polyisocyanate containing uretone imine groups. The starting materials used in the method of this invention should therefore provide a source of uretone imine groups. A material which provides a good source of uretone imine groups is a uretone imine modified methylene diphenyl diisocyanate (hereinafter MDI). Uretone imine modified MDI may be prepared by any known method. One such method is to heat MDI in the presence of a catalyst, for example, a phosphoester such as triethyl phosphate, at 150° to 220° C. Preferably, such materials will contain from about 20 to about 30 percent uretone imine groups.

PMDI is commercially prepared by phosgenation of mixtures of the corresponding methylene-bridged polyphenyl polyamines. PMDI contains from about 20 to about 85, preferably from about 30 to about 75, percent by weight of MDI: about 3 percent to about 30 percent byproducts and impurities; and the remainder closely related polyisocyanates of higher molecular weight and functionality greater than about 2. The impurities and byproducts consist of a variety of compounds such as chlorine bearing components, isocyanate dimers (uretidine diones), carbodiimides, biurets, capped biurets, and the like. Most importantly, for the purposes of the present invention, PMDI also contains uretone imines, in a concentration of from about 4 percent to about 25 percent.

Like MDI, PMDI can also be heated with an appropriate catalyst to form uretone imine groups. Such uretone imine modified materials are not presently commercially available, but can be used with the present invention. Such materials may be prepared by those skilled in the art of preparing modified polyisocyanates with the same catalysts and conditions used to modify MDI. Those catalysts include compounds such as triethyl phosphate and typical reaction temperatures vary from about 150° to about 220° C.

Toluene diisocyanate (hereinafter TDI) from any source can also be used with the method of the present invention. TDI is commonly prepared by phosgenation of toluene diamines. After phosgenating toluene diamines to form TDI, the product TDI is generally distilled from the reaction mixture. TDI is generally available only in this distilled form. While uretone imine modified TDI or undistilled TDI containing uretone imine groups may be used with the method of the present invention in the same manner as any other uretone imine group containing isocyanate, the general unavailability of such materials dictates that in the usual practice of this invention, TDI can be a component added to the reaction admixture to react with preexisting uretone imine groups from other sources.

In one preferred embodiment of the method of the present invention, any uretone imine modified MDI or PMDI is heated with a catalyst. In another preferred embodiment, unmodified PMDI, containing uretone imine groups, is similarly treated. In yet another embodiment, also preferred, a blend of toluene diisocyanate and PMDI and/or uretone imine modified MDI or PMDI is heated with a catalyst. Hereinafter, for clarity, the term "starting isocyanate" will mean any of these starting materials or combinations thereof.

Hydrogen chloride is the preferred catalyst for the reaction wherein uretone imine groups are converted to 2-imino-4,6-dioxohexahydro-s-triazine groups. Preferably, the hydrogen chloride is anhydrous. The catalyst is preferably added in amounts favorable for the formation of 2-imino-4,6-dioxohexahydro-s-triazine group containing compounds. Preferably, the catalyst level is from about 1,000 to about 20,000, but more preferably from about 2,500 to about 8,000 parts per million (ppm).

The starting isocyanate and catalyst admixture is heated under conditions favorable for forming 2-imino-4,6-dioxohexahydro-s-triazine group containing polyisocyanates. For practice of the method of the present invention, preferably, the temperature range for heating the starting isocyanate and catalyst admixture is from about 25° C. to about 200° C., but more preferably from about 40° C. to about 75° C. In addition to the conditions already described herein, such as temperature and catalyst level, the method of the present invention includes the common conditions and practices known to those skilled in the art of working with isocyanates. Included in those standard conditions and practices are, for example, protecting the reaction mixture from oxygen contamination, maintaining constant catalyst levels, avoiding localized heating, avoiding moisture contamination, and the like.

After the reaction forming 2-imino-4,6-dioxohexahydro-s-triazine group containing polyisocyanates is complete, the hydrogen chloride catalyst can be removed. Effective means of removing hydrogen chloride from polyisocyanates are well known to those skilled in the art of preparing polyisocyanates and any such means may be used with the present invention. A preferred method of catalyst removal is to admix the 2-imino-4,6-dioxohexahydro-s-triazine modified polyisocyanate of this invention (hereinafter modified polyisocyanate of the present invention) in a ratio of 1:1 with an inert organic solvent, such as chlorobenzene, and reflux at about 145° C. for about one hour, and then vacuum distill off the organic solvent. Preferably, the resulting polyisocyanate will contain less than about 500 ppm hydrogen chloride, and more preferably less than about 200 ppm hydrogen chloride.

Reaction rates, and, therefore, the period of heating the admixture of uretone imine containing polyisocyanate and hydrogen chloride catalyst are dependent upon temperature and catalyst levels. This reaction period may vary from a few hours to a few days. However, the preferred reaction period, for a starting isocyanate/catalyst admixture containing about 5,000 ppm hydrogen chloride catalyst and held at about 50° C., is about 12 to about 72 hours, but preferably about 20 to about 60 hours, and more preferably about 24 to about 30 hours.

The extent of the reaction to form 2-imino-2,4-dioxohexahydro-s-triazine groups may be monitored spectroscopically and the reaction period determined thereby. Uretone imine groups characteristically absorb infrared radiation at 1720 cm$^{-1}$. The 2-imino-2,4-dioxohexahydro-s-triazine compounds of this invention characteristically absorb infrared radiation at 1660 cm$^{-1}$ (strong), 1699 cm$^{-1}$ (strong), and 1745 cm$^{-1}$ (weak) Therefore, the extent of this reaction may be monitored by observing the disappearance of infrared absorption at 1720 cm$^{-1}$ and the appearance of infrared absorption at 1660 cm$^{-1}$, 1699 cm$^{-1}$, and 1745 cm$^{-1}$.

The reaction mixture until the absorbency at the above wavelengths stabilize. Alternatively, the formation of 2-imino-4,6-dioxohexahydro-s-triazine compounds and disappearance of uretone imine compounds may be determined by other analytical methods known to those skilled in the art, such as high pressure liquid chromotography or carbon ($C^{13}$) nuclear magnetic resonance spectroscopy.

Uretone imine concentration may also be calculated using the general methods above. For example, in an infrared method, an isocyanate sample can be dissolved in chloroform and analyzed for absorption at 1720 $cm^{-1}$ as described above. Uretone imine concentration is then determined by multiplying absorbance at 1720 $cm^{-1}$ by an appropriate extinction coefficient. The extinction coefficient may be determined using any suitable model compound. The model compound, triphenyl uretone imine, was used to determine the extinction coefficient for the present invention.

The polyisocyanate containing 2-imino-4,6-dioxohexahydro-s-triazine groups prepared by the method of the present invention (hereinafter modified polyisocyanate) is also an aspect of the present invention and has improved viscosity stability relative to conventional polyisocyanates. Conventional polyisocyanates tend to increase in viscosity during storage. The extent and rate of this increase is a function of a number of variables, including initial viscosity, acidity, method of production, storage conditions, etc., but generally, commercially available conventional polyisocyanates display this viscosity growth during storage. In general, to be commercially successful, a polyisocyanate should increase in viscosity no more than 20 percent per month when stored at 50° C. Isocyanates with this type of viscosity growth rate have shelf lives of about 6 months. Where a modified polyisocyanate of the present invention is diluted with MDI such that it has an isocyanate equivalent weight and an initial viscosity similar to that of a conventional PMDI material, the polyisocyanate-MDI blend will desirably have less than about 75, preferably less than about 50, and more preferably less than about 40 percent of the viscosity growth of the conventional polyisocyanate. Such a material is defined herein as "viscosity stable".

A modified polyisocyanate of the present invention is higher in viscosity than the starting isocyanate, yet is suitably used without dilution, for instance, to prepare a foam. However, this material can be blended with another isocyanate group containing material in an amount sufficient to achieve a preselected viscosity. This blend is also an aspect of the present invention. The isocyanate group containing material used for dilution is suitably any, preferably liquid, organic isocyanate compound having an average of more than one isocyanate group per molecule. The isocyanate group containing material is suitably crude or distilled, and has a viscosity less than that of the modified polyisocyanate. Such isocyanate group containing compounds are well known and readily available commercially.

Examples of suitable materials useful for dilution of the modified polyisocyanates to prepare the blends of the present invention include aromatic, aliphatic and cycloaliphatic polyisocyanates and combinations thereof. Representative polyisocyanates include diisocyanates such as m-phenylene diisocyanate, toluene-2,4-diisocyanate, toluene-2,6-diisocyanate, hexamethylenediisocyanate, tetra-methylenediisocyanate, cyclohexane-1,4-diisocyanate, hexahydrotoluene diisocyanate and isomers thereof, 1-methoxyphenyl-2,4-diisocyanate, diphenylmethane-4,4'-diisocyanate, diphenylmethane-2,4'-diisocyanate, 3,3'-dimethyl-4,4'-biphenyl diisocyanate, 3,3'-dimethyldiphenyl-methane-4,4'-diisocyanate and the like: triisocyanates such as 4,4',4"-triphenylmethane triisocyanate, toluene-2,4,6-triisocyanate, and the like; tetraisocyanates such as 4,4'-dimethyldiphenylmethane-2,2',5,5'-tetraisocyanate, 4,4'-dicyclohexanediisocyanate, isophorone diisocyanate, isomers of each and the like; other polyisocyanates such as polyphenylisocyanate and the like; and mixtures thereof. TDI, diphenylmethane-4,4'-diisocyanate, diphenylmethane-2,4'-diisocyanate and mixtures thereof are preferred.

The blends of the present invention are composed of from about 1 to about 99 percent by weight modified polyisocyanate of the present invention, and the remainder other isocyanate group containing materials. The relative proportions of the components of the blend are generally selected to achieve a preselected viscosity and preselected properties in resulting products. Advantageously, the relative proportions of the invention and other isocyanate group containing materials are selected to achieve a viscosity suitable for a use of the blend.

Advantageously, for use in making foams, the blends of the present invention have a viscosity of less than about 10,000 centipoise, preferably from about 30 to about 5,000 centipoise, more preferably from about 40 to about 2,500 centipoise. When a blend is to be used for a specific application, the viscosity is most preferably preselected for convenience in preparing that type of material by processes known to those skilled in the art. For instance, in the case of insulative polyurethane foams, viscosity is generally preferably from about 150 to about 3,000 centipoise.

The blends of the invention are suitably used to make polyisocyanurate, polyurethane, polyurea, and polyurethane-polyurea polymers and the like. These polymers are also a part of the present invention and suitably take the form of products such as flexible or rigid foams, adhesives, binders and the like. Polyisocyanurate foams are foams formed using a ratio of isocyanate groups to active hydrogen groups of at least about 1.3, preferably, in the presence of trimerization catalysts. Polyurethane foams are formed when the ratio of isocyanates groups to active hydrogen groups is about 1.0 and polymer formation is primarily due to the reaction of active hydrogen groups of an active hydrogen component with isocyanate groups of a polyisocyanate component. Polyurea foams are formed when polymer formation is due to the reaction of the isocyanate groups of polyisocyanates with the amine groups of polyamines or in the presence of water and this water is used as a carbon dioxide generating additive.

The modified polyisocyanate or blends of the present invention are advantageously reacted with active hydrogen compounds. Any suitable organic compound containing an active hydrogen containing group, as determined by the Zerewitinoff method, may be used for reaction with the invention or blends thereof with other isocyanate group containing materials. Active hydrogen compounds are compounds having hydrogen-containing functional groups which will react with an isocyanate group. The Zerewitinoff test described by Kohler in the *Journal of the American Chemical Society*, Vol. 49, page 3181 (1927) predicts the tendency of a hydrogen-containing group to react with isocyanates.

Active hydrogen components most commonly used in polyurethane production are those compounds having at least two hydroxyl groups per molecule. Those compounds are referred to herein as polyols. Representatives of suitable polyols are generally known and are described in such publications as *High Polymers*, Vol. XVI, "Polyurethanes, Chemistry and Technology" by Saunders and Frisch, Interscience Publishers, New York, Vol. I, pp. 32-42, 44-54 (1962) and Vol. II, pp. 5-6, 198-199 (1964); *Organic Polymer Chemistry* by K. J. Saunders, Chapman and Hall, London, pp. 323-325 (1973); and *Developments in Polyurethanes*, Vol. I, J. M. Burst, ed., Applied Science Publishers, pp. 1-76 (1978).

Typical polyols include polyester polyols, polyester amide polyols, and polyether polyols having at least two hydroxyl groups. Polyethers and polyesters having hydroxyl terminated chains are preferred for use as relatively high molecular weight active hydrogen containing compounds for use in forming polyurethanes in particular. Examples of polyols also include hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers, including polythioethers and acetals, such as polyacetals. Aminated polyols may also be used. Compounds wherein the active hydrogen containing groups are amine groups are also suitably used with this invention.

The modified polyisocyanate of the present invention is advantageously reacted with active hydrogen compounds to form polymers in the presence of a blowing agent. Any blowing agent or mixture thereof is suitable for use in the practice of the invention. Suitable blowing agents include inorganic blowing additives such as water, organic blowing agents which are volatile at reaction temperatures, and dissolved inert gases. Suitable organic blowing agents include acetone; ethyl acetate: halogen-substituted alkanes such as methylene chloride, chloroform, ethylidene chloride, vinylidene chloride, monofluorotrichloromethane, chlorodifluoromethane, dichlorodifluoromethane and the like: butane: pentane; hexane; heptane: diethyl ether: and the like. Gases inert to the starting components such as nitrogen, air, carbon dioxide and the like are also useful blowing agents. Compounds, such as azides, which decompose at suitable temperatures to produce gases such as nitrogen are also useful. Of the hydrochlorofluorocarbon and perfluorocarbon blowing agents, HCFC 123 and HCFC 141 B are commonly used to substitute for chlorofluorocarbons which contain no hydrogens and are available commercially from Du Pont ® and Allied Signal ®. Preferred blowing agents are compounds which boil between about −50° C. and about 100° C., more preferably between about 0° C. and about 50° C.

The amount of blowing agent or additive employed is not critical to the invention, but is preferably sufficient to foam the reaction mixture. The amount will vary with factors such as the density desired in a foamed product.

Water is a useful blowing agent for use with the present invention. In addition to generating carbon dioxide gas for foaming, water reacts quickly with polyisocyanate components, thus contributing to early polymer strength needed for gas retention. Generally, when water is used, it is present in proportions of from about 1.5 to about 8 weight percent of water based on total weight of active hydrogen components. Other blowing agents and additives, can be used with water.

Rigid polyisocyanurate and polyurethane foams prepared with the polymers of the present invention are particularly useful. Those skilled in the art of preparing such foams can readily use the modified polyisocyanate or blends of the present invention to prepare foams. Methods known to those skilled in the art include, for instance, the process of U.S. Pat. No. 4,604,410, can be followed, substituting the modified polyisocyanates of the present invention, or blends of the invention, for referenced polyisocyanates. Preferably, the invention, or blends of the invention, are reacted with a polyfunctional active hydrogen compound, in the presence of a catalyst which catalyzes the formation of isocyanurates or urethanes, and a blowing agent suitable for forming foams having preselected physical properties.

Suitable catalysts for use with the present invention include those which catalyze the formation of isocyanurates such as those mentioned in Saunders and Frisch, *Polyurethanes, Chemistry and Technology* in 1 *High Polymers* Vol. XVI, pp. 94-97 (1962). Such catalysts are referred to herein as trimerization catalysts. Examples of these catalysts include aliphatic and aromatic tertiary amine compounds, organometallic compounds, alkali metal salts of carboxylic acids, phenols and symmetrical triazine derivatives. Preferred catalysts are potassium salts of carboxylic acids such as potassium octoate and tertiary amines such as, for instance, 2,4,6-tris(dimethyl aminomethyl) phenol.

Polyurethane catalysts are also suitably used with the present invention. The catalyst is preferably incorporated in the formulation in an amount suitable to increase the rate of reaction between the isocyanate groups of the composition of the present invention and a hydroxyl-reacting species. Although a wide variety of materials is known to be useful for this purpose, the most widely used and preferred catalysts are the tertiary amine catalysts and the organotin catalysts.

Examples of the tertiary amine catalysts include, for example, triethylenediamine, N-methyl morpholine, N-ethyl morpholine, diethyl ethanolamine, N-coco morpholine, 1-methyl-4-dimethylaminoethyl piperazine, 3-methoxy-N-dimethylpropylamine, N,N-diethyl-3-diethyl aminopropylamine, dimethylbenzyl amine and the like. Tertiary amine catalysts are advantageously employed in an amount from about 0.01 to about 2 percent by weight of the polyol formulation.

Examples of organotin catalysts include dimethyltin dilaurate, dibutyltin dilaurate, dioctyltin dilaurate, stannous octoate and the like. Other examples of effective catalysts include those taught in, for example, U.S. Pat. No. 2,846,408. Preferably the organotin catalyst is employed in an amount from about 0.001 to about 0.5 percent by weight of the the polyol formulation.

The polymers of the present invention, when foamed, may produce less smoke and have better flammability properties than foams of otherwise identical formulations prepared with conventional polyisocyanates. For example, in foams prepared with both chlorofluorocarbon and carbon dioxide blowing additives, the modified polyisocyanates of the present invention can be used to prepare a foam which produces about 25 percent less smoke than a similar foam prepared with a conventional polyisocyanate. Where water is used as a blowing additive, the present invention can be used to prepare a foam which produces about 30 percent less smoke than a similar foam prepared with conventional polyisocyanates. Therefore, foams may be prepared with polymers of the present invention with substantially reduced chlorofluorocarbon levels without undesirable reduction of desired flammability properties.

Foams produced with the modified polyisocyanates of the present invention also may have improved dimensional stability compared to foams produced with conventional polyisocyanates. For example, a foam prepared with a conventional PMDI material expands about 12 percent after 28 days' storage at 158° F. and 100 percent relative humidity, while a foam prepared with the modified polyisocyanates of the present invention expands only about 6 percent.

Also a part of the invention is the family of compounds consisting of a 2-imino-4,6-dioxohexahydro-s-triazine group, wherein each nitrogen is bonded to a fragment of TDI, MDI, or PMDI. The term "fragment" is defined herein as the residue of a TDI, MDI, or PMDI molecule which is missing one isocyanate group and bonded to the 2-imino-4,6-dioxohexahydro-s-triazine group at the location of the missing isocyanate group. These fragments result from reactions of MDI and/or PMDI to combine and form a uretone imine and then the reaction of MDI, PMDI, and/or TDI with the uretone imine to form the claimed family of compounds, wherein the "missing" isocyanate groups of the fragments are incorporated into the structure of the 2-imino-4,6-dioxohexahydro-s-triazine group. For example, although in the practice of the present invention these fragments are selected independently, one configuration is 1-isocyanatotolyl-3,5-di-(isocyanatobenzylphenyl)-2-isocyanotobenzyl-phenylimino-4,6-dioxohexahydro-s-triazine. The compounds of the present invention have a functionality of greater than or equal to 4.

TEST METHODS USEFUL IN THE PRACTICE OF THE INVENTION

Acidity Determination

The practice of the method of this invention requires that hydrogen chloride be added to a polyisocyanate material. Hydrogen chloride concentration in polyisocyanates may be measured as acidity by any suitable method. A preferred method for measuring acidity consists of placing from about 2 to about 10 grams of a polyisocyanate sample into a beaker. The sample is first dissolved by stirring with 75 milliliters of toluene and methanol 1:1, then the sample is further diluted with another 75 milliliters of toluene and methanol 1:1. The beaker is covered with a watch glass and placed on a hot plate set for about 230° C. The solution in the beaker is stirred and heated for exactly 7 minutes. The solution should be boiling for about the last two minutes of the heating period. The beaker is then removed from the hot plate. The solution in the beaker may be titrated by any suitable means, for instance, by use of an autotitrator. The titrant is preferably 0.03N potassium hydroxide. The resultant titration should produce an "S" shaped curve. A blank is then run under the same conditions and the volume (V) of titrant consumed is determined. Parts per million (ppm) hydrogen chloride is calculated using the formula:

$$\text{ppm hydrogen chloride} = ((V-B) \times N \times 3.65) \times (1/S) \times (1 \times 10^4))$$

wherein V represents the milliliters of potassium hydroxide titrant consumed by the sample; B represents the milliliters of titrant consumed by the blank; N represents the normality of the titrant; and S represents the weight in grams of the isocyanate material placed into the beaker.

SMOKE AND HEAT RELEASE DETERMINATION

Foams prepared with the present invention may exhibit improved flammability properties. These properties may be measured with any acceptable method. One method is to measure the smoke and heat released during combustion. This may be done by ASTM E-906-83 titled "Standard Test Method for Heat and Visible Smoke Release for Materials and Products". In this test, a sample of foam is exposed to metered radiation from an electrical heating element. This occurs inside a special testing apparatus where the sample is exposed to a constant stream of air. Air exiting the apparatus is monitored for smoke particles and changes in optical density. Heat released by the burning foam is measured with a calibrated radiometer. Ignition is accomplished by a point ignition of the surface.

DIMENSIONAL STABILITY DETERMINATION

Foams prepared with the present invention also may exhibit improved dimensional stability properties. These properties may also be tested by any acceptable means, and ASTM D-2126-87 titled "Standard Test Method for Response of Rigid Cellular Plastics to Thermal and Humid Aging" is such a means. In this test, test specimens are machined or sawed from samples so as to have smooth faces and edges, free of cracks, and be 100 millimeters × 25 millimeters × 25 millimeters in dimension. Specimens are subjected to a standard set of conditions, such as 23°±2° C. and 50±5 percent relative humidity, at least overnight to condition the specimens for testing. Prior to testing and after conditioning, mass is determined to the nearest 0.05 percent and dimensions are determined to the nearest 0.1 percent. The specimens are then exposed to one of many sets of standard conditions, e.g., 23°±3° C. and 50±5 percent relative humidity, 70°±2° C. and 95±3 percent relative humidity, etc., for 24 hours, 168 hours, and 336 hours. Specimens are conditioned for 2 hours under ambient conditions. The specimens are remeasured and reweighed and changes noted.

The following examples and comparative examples serve to illustrate the present invention. These examples are included for illustrative purposes only and are not intended to limit the scope of the invention.

EXAMPLE 1

About 200 g of uretone imine modified MDI are placed into a flask equipped to provide a constant temperature and continuous stirring. Anhydrous hydrogen chloride is bubbled into the uretone imine modified MDI at ambient temperature until the desired level, 3,500 ppm, is reached. The catalyst-isocyanate mixture is heated at 50° C. and samples are removed periodically for analysis. At the beginning of this experiment, the uretone imine concentration is 25 percent. After one day, the uretone imine concentration is 3.4 percent. After two days, the uretone imine concentration is 1.0 percent. After 5 days, the uretone imine concentration is 0.0 percent.

EXAMPLE 2

About 400 g of PMDI are placed into a flask equipped to provide a constant temperature and continuous stirring. A quantity of the PMDI is retained and isolated as a control. Anhydrous hydrogen chloride is bubbled into the PMDI at ambient temperature until the desired level, 5,540 ppm, is reached. The catalyst-isocyanate mixture is heated at 50° C. for 24 hours. At the conclusion of the heating, the hydrogen chloride catalyst is removed by stripping until acidity concentration is about the same as the control. At the beginning of the experiment, the PMDI has a uretone imine concentration of 9.6 percent. At the conclusion of the experiment, the uretone imine concentration is about 0 percent. A quantity of the control and a quantity of the reaction product diluted to about the same viscosity with MDI are stored at 50° C. for twenty weeks. Samples are taken periodically. Viscosity is determined using a Cannon-Fenske viscometer at 25° C. The results are recorded in Table 1.

EXAMPLE 3

The method of Example 2 is substantially reproduced except that the PMDI has an initial uretone imine concentration of 17.6 percent, the catalyst concentration is 5,500 ppm. The results are recorded in Table 2.

TABLE 1

| STORAGE TIME IN WEEKS AT 50° C. | CONTROL* VISCOSITY IN CENTIPOISE | MODIFIED PMDI — VISCOSITY IN CENTIPOISE |
| --- | --- | --- |
| 0 | 168 | 168 |
| 5 | 206 | 195 |
| 12 | 245 | 198 |
| 20 | 305 | 224 |
| PERCENT INCREASE PER MONTH | 17.6 | 7.2 |

*Not an example of the invention

TABLE 2

| STORAGE TIME IN WEEKS AT 50° C. | CONTROL* VISCOSITY IN CENTIPOISE | MODIFIED PMDI — VISCOSITY IN CENTIPOISE |
| --- | --- | --- |
| 0 | 721 | 730 |
| 5 | 939 | 870 |
| 12 | 1166 | 960 |
| 20 | 1340 | 1020 |
| PERCENT INCREASE PER MONTH | 18.6 | 8.6 |

*Not an example of the invention

EXAMPLE 4

Two polyisocyanurate foams are prepared using the following formulation: an "A" component consisting of 200 parts polyisocyanate and 1.5 parts surfactant; and a "B" component consisting of 31 parts polyester polyol, 3 parts polyether polyol, 1 part surfactant, 4 parts epoxy resin, 0.5 part urethane catalyst, 6 parts trimerization catalyst, and 12.5 parts carbon dioxide blowing agent (8 parts ethylhexanoic acid and 2.5 parts water and 2.0 parts triethyl phosphate). In one foam, the polyisocyanate is a conventional PMDI and is used as a control. In the other foam, the polyisocyanate is the same PMDI as is used for the control, except it has been treated by the method of the present invention. The control foam made with conventional PMDI is analyzed for smoke production and receives a value of 983. The foam prepared with the modified polyisocyanate of the present invention is analyzed for smoke production and receives a value of 698. The control foam is analyzed for heat release and receives a value of 479 watts per square centimeter. The foam prepared with the polymer of the present invention is analyzed for heat release and receives a value of 325 watts per square centimeter.

EXAMPLE 5

Two polyurethane foams are prepared using the following formulation: an "A" component consisting of a polyisocyanate, and a "B" component consisting of 100 parts polyether polyol, 1.5 parts surfactant, 1.6 parts urethane catalyst, and 40 parts trichlorofluorocarbon blowing agent. In one foam used as a control, the "A" component consists of a conventional PMDI. In the other foam, the "A" component is the same conventional PMDI as is used for the control, except it has been treated by the method of the present invention and then diluted with MDI to its pretreatment viscosity. Both foams are tested for dimensional stability at 158° F. and 100 percent relative humidity. The control foam increases in volume by 11.6 percent in 28 days, while the foam prepared with the present invention increases only 5.7 percent.

What is claimed is:

1. A method for preparing a liquid polymeric isocyanate comprising heating an admixture of a polyisocyanate containing uretone imine groups and a catalyst under reaction conditions sufficient to form compounds containing 2-imino-4,6-dioxohexahydro-s-triazine groups.

2. The method of claim 1 wherein the liquid polymeric isocyanate is viscosity-stable.

3. The method of claim 1 wherein the catalyst is hydrogen chloride.

4. The method of claim 1 further comprising removing the catalyst by stripping.

5. The method of claim 1 wherein the catalyst concentration is from about 1,000 to about 20,000 ppm.

6. The method of claim 1 wherein the catalyst concentration is from about 2,500 to about 8,000 ppm.

7. The method of claim 1 wherein the admixture is heated at a temperature form about 25° C. to about 200° C.

8. The method of claim 7 wherein the temperature is from about 40° C. to about 75° C.

9. The method of claim 1 wherein the admixture is heated for from about 12 to about 72 hours.

10. The method of claim 1 wherein the admixture is heated for from about 24 to about 30 hours.

11. The method of claim 1 wherein the polyisocyanate is selected from uretone imine modified polymethylene polyphenylisocyanate, uretone imine modified methylene diphenyl diisocyanate, polymethylene polyphenylisocyanate or mixtures thereof.

12. The method of claim 1 wherein the reaction admixture further contains toluene diisocyanate.

13. A polyisocyanate composition comprising a liquid polyisocyanate containing compounds which have the general formula:

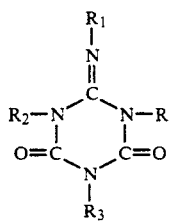

wherein R, $R_1$, $R_2$, and $R_3$ are independently selected form the group consisting of:

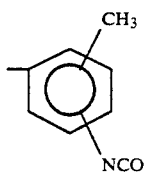

(a)

and

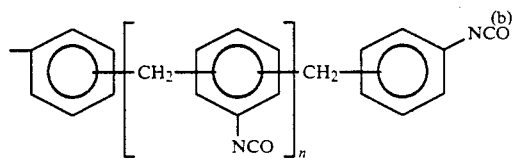

(b)

wherein n is an integer from 0 to 4 inclusive.

14. The composition of claim 13 wherein the polyisocyanate is viscosity stable.

15. The composition of claim 14 wherein the viscosity-stabilized polyisocyanate further comprises a blend with a conventional diisocyanate or polyisocyanate.

16. A polymer prepared by reacting a reaction mixture comprising as components:
(a) an active hydrogen group containing compound; and
(b) a polyisocyanate component containing from about 1 to about 100 weight percent of a polyisocyanate containing compounds which have the general formula:

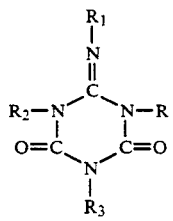

wherein R, $R_1$, $R_2$, and $R_3$ are independently selected from the group consisting of:

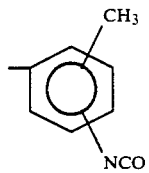

(a)

and

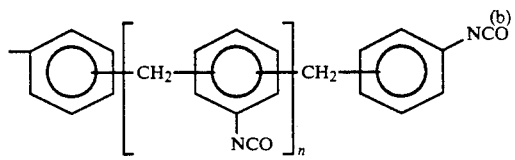

(b)

wherein n is an integer from 0 to 4 inclusive.

17. The polymer of claim 16 wherein the polymer is a foam and the reaction mixture further comprises a blowing agent, or a blowing agent and a catalyst.

18. The polymer of claim 17 having improved flammability or dimensional stability properties.

19. Compounds of the general formula:

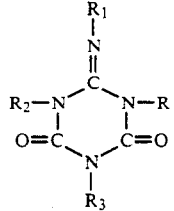

wherein R, $R_1$, $R_2$, and $R_3$ are independently selected from the group consisting of:

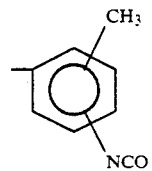

(a)

and

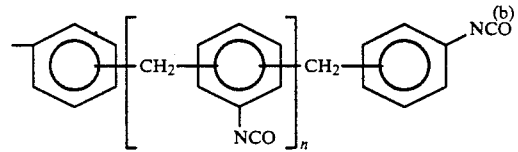

(b)

wherein n is an integer from 0 to 4 inclusive.

* * * * *